US008039010B2

(12) United States Patent
Trogden et al.

(10) Patent No.: US 8,039,010 B2
(45) Date of Patent: Oct. 18, 2011

(54) SUSTAINED RELEASE INTRAOCULAR DRUG DELIVERY SYSTEMS COMPRISING A WATER SOLUBLE THERAPEUTIC AGENT AND A RELEASE MODIFIER

(75) Inventors: John T. Trogden, Anaheim, CA (US); Robert T. Lyons, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/556,503

(22) Filed: Nov. 3, 2006

(65) Prior Publication Data

US 2008/0107694 A1     May 8, 2008

(51) Int. Cl.
*A61K 38/00* (2006.01)
*A61K 31/71* (2006.01)
*A61K 9/00* (2006.01)
*A61K 47/00* (2006.01)
*A61K 39/95* (2006.01)
*A61P 27/00* (2006.01)

(52) U.S. Cl. .................. 424/400; 424/145.1; 424/130.1; 514/2; 514/44 R; 514/772

(58) Field of Classification Search .................. None
See application file for complete search history.

(56) References Cited

U.S. PATENT DOCUMENTS

| | | | |
|---|---|---|---|
| 4,521,210 A | 6/1985 | Wong | |
| 4,853,224 A | 8/1989 | Wong | |
| 4,997,652 A | 3/1991 | Wong | |
| 5,164,188 A | 11/1992 | Wong | |
| 5,443,505 A | 8/1995 | Wong | |
| 5,501,856 A | 3/1996 | Ohtori | |
| 5,766,242 A | 6/1998 | Wong | |
| 5,824,072 A | 10/1998 | Wong | |
| 5,869,079 A | 2/1999 | Wong | |
| 6,074,661 A | 6/2000 | Olejnik | |
| 6,248,345 B1* | 6/2001 | Goldenheim et al. | 424/426 |
| 6,331,313 B1 | 12/2001 | Wong | |
| 6,369,116 B1 | 4/2002 | Wong | |
| 6,699,493 B2 | 3/2004 | Wong | |
| 6,713,081 B2 | 3/2004 | Robinson | |
| 6,818,447 B1 | 11/2004 | Pavco | |
| 6,899,717 B2 | 5/2005 | Weber | |
| 7,048,946 B1 | 5/2006 | Wong | |
| 7,090,681 B2 | 8/2006 | Weber | |
| 2004/0054374 A1 | 3/2004 | Weber | |
| 2004/0138163 A1* | 7/2004 | McSwiggen et al. | 514/44 |
| 2004/0170665 A1 | 9/2004 | Donovan | |
| 2005/0196421 A1* | 9/2005 | Hunter et al. | 424/423 |
| 2006/0020044 A1* | 1/2006 | Berlin | 514/724 |
| 2006/0121085 A1 | 6/2006 | Warren et al. | 424/426 |
| 2006/0182783 A1* | 8/2006 | Hughes et al. | 424/427 |
| 2006/0210604 A1 | 9/2006 | Dadey et al. | 424/427 |
| 2006/0216242 A1* | 9/2006 | Rohloff et al. | 424/45 |
| 2009/0226531 A1* | 9/2009 | Lyons et al. | 424/501 |
| 2009/0258924 A1* | 10/2009 | Lyons et al. | 514/44 A |
| 2010/0311808 A1 | 12/2010 | Lyons et al. | |

FOREIGN PATENT DOCUMENTS

| | | |
|---|---|---|
| WO | WO 94/14417 | 7/1994 |
| WO | WO 95/35097 | 12/1995 |
| WO | WO 2004/081196 | 9/2004 |
| WO | WO 2006/041942 | 9/2004 |
| WO | WO 2005/110362 | 11/2005 |
| WO | WO 2006/053175 | 5/2006 |

OTHER PUBLICATIONS

Van Wijngaarden et al. (JAMA. Mar. 23/30, 2005; 293(12): 1509-1513).*
Stone et al (N Engl J Med. Oct. 5, 2006, 355(14): 1493-1495).*
Boehringer-Ingelheim (Specification Sheets for RG-752; 2006; Inherent Viscosity and MW for RG-752).*
Schwach et al (European Journal of Pharmaceutics and Biopharmaceutics. 2003; 56: 327-336).*
Carrasquillo al (Investigative Opthalmology & Visual Science. Jan. 2003; 44(1): 290-299).*
U.S. Appl. No. 10/917,909, filed Aug. 13, 2004, Weber.
U.S. Appl. No. 11/370,301, filed Mar. 8, 2006, Hughes.
U.S. Appl. No. 11/364,687, filed Feb. 27, 2006, Hughes.
U.S. Appl. No. 11/116,698, filed Apr. 27, 2005, Hughes.
U.S. Appl. No. 11/021,947, filed Dec. 23, 2004, Weber.
Carrasquillo K. et al., *Controlled delivery of the anti-VEGF aptamer EYE001 with poly(lactic-co-glycolic)acid microspheres*, IOVS Jan. 2003 44(1).
Gaudreault et al., *Preclinical pharmacokinetics of ranibizumab (rhuFabV2) after a single intravitreal administration*, IOVS, (2005); 46(2):726-733.
Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.
Jackson J. et al., *The encapsulation of ribozymes in biodegradable polymeric matrices*, Int J of Pharmaceutics 243 (2002) 43-55.
Khan A. et al., *Sustained polymeric delivery of gene silencing antisense ODNs, siRNA, DNAzymes and ribozymes: in vitro and in vivo studies*, J Drug Target, Jul. 12, 2004(6), pp. 393-404.
Rosa G., et al., *A new delivery system for antisense therapy: PLGA microspheres encapsulating olignucleotide/polyethyleneimine solid complexes*, Int J of Pharmaceutics 254 (2003) 89-93.

* cited by examiner

*Primary Examiner* — Scott Long (74) *Attorney, Agent, or Firm* — Louis V. Wollenberge; Joel B. German; Debra D. Condino (57) ABSTRACT

A biocompatible, sustained release intraocular drug delivery system comprising a protein or polynucleotide therapeutic agent, a polymeric carrier for the therapeutic agent and a long chain fatty alcohol release modifier. The biocompatible, sustained release intraocular drug delivery system can be used to treat an ocular condition.

8 Claims, 1 Drawing Sheet

Figure 1

SUSTAINED RELEASE INTRAOCULAR DRUG DELIVERY SYSTEMS COMPRISING A WATER SOLUBLE THERAPEUTIC AGENT AND A RELEASE MODIFIER

BACKGROUND

The present invention relates to sustained release drug delivery systems and methods for therapeutic use of the sustained release drug delivery systems. In particular, the present invention relates to sustained release drug delivery systems containing a water soluble therapeutic agent and a release modifier to modify the rate of release of the therapeutic agent from the drug delivery system, and methods for making and using such drug delivery systems. The drug delivery systems disclosed herein can be used for example in methods for treating an ocular condition of a patient.

Various therapeutic agents (such as proteins and polynucleotides) have been used to treat an ocular condition. A difficulty with administration of a therapeutic agent to treat an ocular condition includes being able to appropriately deliver the therapeutic agent in proximity to the desired target tissue. For the treatment of a retinal condition such as macular edema or macular degeneration the target tissue can be the retina or the macula. For the treatment of glaucoma the target tissue can be the ciliary body or photoreceptors of the retina. When a therapeutic agent is not delivered in proximity to the target tissue, for example when a topical pharmaceutical (i.e. an eye drop) is administered to the cornea of eye in order to treat a target tissue within the anterior chamber or the posterior chamber, the therapeutic agent can arrive at the target site in a sub-therapeutic amount and with undesirable side effects upon other tissues. Side effects can include undesirable systemic effects which can result when a relatively large amount of the therapeutic agent is administered, so that a therapeutic amount of the therapeutic agent can be present after administration at the target tissue site. Ocular side effects, such as cataract formation and elevated intraocular pressure, can also result when the therapeutic agent is not administered at a location proximate to the target tissue site.

Another difficulty with administration of a therapeutic agent to treat an ocular condition can result from the desirability of maintaining a therapeutically effective amount of the therapeutic agent proximate to the target tissue for a prolonged period of time, such as for several weeks or months. Thus, because topical formulations of therapeutic agents or aqueous injectables thereof typically disperse, diffuse or are degraded to subtherapeutic levels of the therapeutic agent in a matter of minutes or hours, frequent re-dosing is therefore required to treat a chronic ocular condition.

Sustained release drug delivery systems are known. For example U.S. Pat. No. 6,713,081 discloses polyvinyl alcohol intraocular implants. See also U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493 and U.S. patent publication 20040170665.

Additionally, release of protein or polynucleotide therapeutic agent from a sustained release drug delivery system is known. See e.g. Jackson J. et al., *The encapsulation of ribozymes in biodegradable polymeric matrices*, Int J of Pharmaceutics 243 (2002) 43-55, discusses sustained release formulations of ribozymes comprising injectable PLA and PLGA microspheres or a polycaprolactone paste. Jackson suggests controlling the release rate by altering the ribozyme loading. Rosa G., et al., *A new delivery system for antisense therapy: PLGA microspheres encapsulating oligonucleotide/ polyethyleneimine solid complexes*, Int J of Pharmaceutics 254 (2003) 89-93, discloses antisense oligonucleotide PLGA microspheres wherein the in vitro release profile can be changed by changing the nitrogen/phosphate ratio of a polyethylenimine used, drug load or the type of PLGA used. Carrasquillo K. et al., *Controlled delivery of the anti-VEGF aptamer EYE001 with poly(lactic-co-glycolic)acid microspheres*, IOVS January 2003 44(1), discusses anti-VEGF PLGA microspheres. Khan A. et al., *Sustained polymeric delivery of gene silencing antisense ODNs, siRNA, DNAzymes and ribozymes: in vitro and in vivo studies*, discusses PLGA microspheres of siRNAs, oligonucleotides, ribozymes and DNAzymes, including one or more of these molecules with an attached lipophilic group to change the release rate. Additionally, see also U.S. patent application Ser. Nos. 11/116,698; 11/364,687, and 11/370,301.

A problem with known sustained release drug delivery systems includes burst release of the therapeutic agent from the drug delivery system. A burst release occurs when more than about 30% of the therapeutic agent contained by the drug delivery system is released from the drug delivery system within about 48 hours after in vivo or in vitro placement (by injection or implantation) of the drug delivery system. Burst release can be a particular problem with water soluble drugs which have a propensity to quickly enter solution in an aqueous physiological environment. A water-soluble therapeutic agent (a therapeutic agent can be referred to synonymously as a drug) is defined as a drug of which 10 mg or more can enter solution in one ml of water at room temperature (20 degrees C.). A slightly or sparingly soluble drug has the property that only from 1 mg to 10 mg of the drug can form a solution in one ml of water at room temperature. A poorly soluble drug has the property that only less than 1 mg of the drug can form a solution in one ml of water at room temperature. Water soluble drugs can include proteins and polynucleotides. Sirna-027, is a highly water-soluble duplex siRNA that can form aqueous solutions of up to 500 mg/mL. A protein can be defined as a polypeptide which comprises two or more amino acid resides and a polynucleotide can be defined as a compound which comprises two or more nucleotides.

It is known to use a release modifier in a drug delivery system so as to modify the rate at which a therapeutic agent is released from the drug delivery system. See eg U.S. Pat. No. 7,048,946.

Aliphatic Alcohols

Aliphatic alcohols (also known synonymously as fatty alcohols or as long chain alcohols or as long chain fatty alcohols) are predominately straight chain organic molecules with an even number of carbon atoms derived from natural fats and oils. Aliphatic alcohols can be converted to or derived from fatty acids and fatty aldehydes. It is known to use the smaller aliphatic alcohols as additives in cosmetics and food, and as industrial solvents. Some larger aliphatic alcohols have been used as biofuels.

Due to their amphipathic nature, aliphatic alcohols can behave as nonionic surfactants and find use as emulsifiers, emollients and thickeners in the cosmetics and food industries. Additionally, aliphatic alcohols are a common component of waxes, mostly as esters with fatty acids but also as alcohols themselves.

Natural Fatty alcohols can be derived from natural fats and oils and are high molecular straight chain primary alcohols. They include lauryl (C12), myristyl (C14), Cetyl (or palmityl: C16), stearyl (C18), Oleyl (C18, unsaturated), and Linoleyl (C18, polyunsaturated) alcohols. Synthetic fatty alcohols equivalent physically and chemically to natural alcohols can be obtained from oleochemical sources such as coconut and palm kernel oil. Fatty alcohols have been used as emulsifiers and emollients in skin creams, as well a as chemical intermediates. An important use of fatty alcohols is as raw material for the production of fatty sulfate salts and alcohol ethoxylates for foaming and cleaning purposes in the detergent industry. Chemical reactions of primary alcohols include esterifications, ethoxylation, sulfation, oxidation and many other reactions. Derivatives of fatty alcohols and their end use applications include nonionic surfactants (ethoxylates and propoxylates); anionic surfactants (alkyl sulfates and alkyl ethoxy sulfates); chemical intermediates and polymerization modifiers (alkyl halides, alkyl mercaptans); quaternary ammonium compounds for detergent sanitisers, softeners for textiles, phase transfer catalyst and biocides; antioxidants for plastics (alkyl thiopropionates and alkyl phosphites); lubricant additives (metallic and thio alkylphosphates); flavor and fragrance (aldehydes and ketones); PVC plasticizers (dialkyl Phthalates, adipates and trimellitates); coatings and inks (acrylate and methacrylate esters), and; water treatment (acrylate and methacrylate esters) Large amount of fatty alcohols are used as special solvents, fillers in plasticizer and insulating materials for the building industry. Fatty alcohols are used as ingredients in the industries of agricultural, foodstuff, metal processing, cosmetics, lube additive, pharmaceutical, rubber, textile, perfume and flavoring as well as synthetic detergent.

Aliphatic alcohols include:
capryl alcohol (1-octanol)—8 carbon atoms
pelargonic alcohol (1-nonanol)—9 carbon atoms
capric alcohol (1-decanol, decyl alcohol)—10 carbon atoms
lauryl alcohol (1-dodecanol)—12 carbon atoms
myristyl alcohol (1-tetradecanol)—14 carbon atoms
cetyl alcohol (1-hexadecanol: $C_{16}H_{34}O$)—16 carbon atoms and has a molecular weight of 242.45
palmitoleyl alcohol (cis-9-hexadecan-1-ol)—16 carbon atoms, unsaturated, $CH_3(CH_2)_5CH=CH(CH_2)_8OH$
stearyl alcohol (1-octadecanol)—18 carbon atoms
isostearyl alcohol (16-methylheptadecan-1-ol)—18 carbon atoms, branched, $(CH_3)_2CH-(CH_2)_{15}OH$
elaidyl alcohol (9E-octadecen-1-ol)—18 carbon atoms, unsaturated, $CH_3(CH_2)_7CH=CH(CH_2)_8OH$
oleyl alcohol (cis-9-octadecen-1-ol)—18 carbon atoms, unsaturated
linoleyl alcohol (9Z, 12Z-octadecadien-1-ol)—18 carbon atoms, polyunsaturated
elaidolinoleyl alcohol (9E,12E-octadecadien-1-ol)—18 carbon atoms, polyunsaturated
linolenyl alcohol (9Z,12Z,15Z-octadecatrien-1-ol)—18 carbon atoms, polyunsaturated
elaidolinolenyl alcohol (9E,12E,15-E-octadecatrien-1-ol)—18 carbon atoms, polyunsaturated
ricinoleyl alcohol (12-hydroxy-9-octadecen-1-ol)—18 carbon atoms, unsaturated, diol, $CH_3(CH_2)_5CH(OH)CH_2CH=CH(CH_2)_8OH$
arachidyl alcohol (1-eicosanol)—20 carbon atoms
behenyl alcohol (1-docosanol)—22 carbon atoms
erucyl alcohol (cis-13-docosen-1-ol)—22 carbon atoms, unsaturated, $CH_3(CH_2)_7CH=CH(CH_2)_{12}OH$
lignoceryl alcohol (1-tetracosanol)—24 carbon atoms
ceryl alcohol (1-hexacosanol)—26 carbon atoms
montanyl alcohol, cluytyl alcohol (1-octacosanol)—28 carbon atoms
myricyl alcohol, melissyl alcohol (1-triacontanol)—30 carbon atoms, and;
geddyl alcohol (1-tetratriacontanol)—34 carbon atoms.

Behenyl alcohol, lignoceryl alcohol, ceryl alcohol, 1-heptacosanol, montanyl alcohol, 1-nonacosanol, myricyl alcohol, 1-dotriacontanol, and geddyl alcohol are together classified as policosanol, with montanyl alcohol and myricyl alcohol being the most abundant.

1-eicosanol (arachidyl alcohol) has the formula $CH_3(CH_2)_{18}CH_2OH$ and a molecular weight of 298.55. Synonyms are 1-Icosanol; Icosan-1-ol; Icosanol; arachidic alcohol; eicosyl alcohol; 1-prydroxyeicosane, and; eicosanol-(1). It is a white solid with a melting point of 64-66° C.

What is needed therefore is a sustained release drug delivery system for a water soluble therapeutic agent from which drug delivery system the therapeutic agent can be released without a burst effect.

SUMMARY

The present invention meets this need and provides is a sustained release drug delivery system for a water soluble therapeutic agent from which drug delivery system the therapeutic agent can be released without a burst effect.

Our invention comprises drug delivery systems for extended or sustained drug release into an eye of a therapeutic agent. The drug delivery system can be in the form of implants or microparticles which upon intraocular administration provide a therapeutic amount of the therapeutic agent for an extended time period, such as for at least about one week and for a period of time of up to twelve months.

Our intraocular drug delivery systems comprise a therapeutic agent, a polymeric carrier and a release modifier.

Therapeutic Agents

Therapeutic agents within the scope of our invention are water soluble therapeutic agents, such as proteins and polynucleotides. The term polynucleotide includes oligonucleotides. An oligonucleotide contains 25 or fewer nucleotides. Protein therapeutic agents useful in our invention include peptides, proteins, antibodies, and antibody fragments (such as a monovalent fraction antigen-binding papain fragment (Fab) or a bivalent fraction antigen binding pepsin fragment [F'ab$_2$]), VEGF, monoclonal antibodies (such as Humira [adalimumab) for rheumatoid and psoriatic arthritis], antibody fragments (such as Lucentis [ranibizumab] and Imclone's IMC-1121 Fab for acute macular degeneration ["AMD"]), polyclonal antibodies, and hormones such as human growth hormone (somatotropin).

Oligonucleotide (ONT) therapeutic agents useful in our invention include short interfering ribonucleic acids (siRNAs) such as Sirna-027 (Sirna Therapeutics) and Cand5 (Acuity Pharmaceuticals), oligonucleotide aptamers (single stranded RNA or DNA that binds proteins) such as Macugen (pegaptanib sodium, Genzyme), and microRNA and shRNA (short hairpin RNA). The oligonucleotide therapeutic agent can be a 23-mer (23 bases in a specific sequence). The RNA bases are adenosine, guanosine, uridine, and cytidine. Sirna-027 is a duplex RNA, each chain being a 21-mer (19 base pairs plus two unpaired overhangs).

Preferred drug delivery systems comprise, for example, a polymeric solid insertable drug delivery device. Preferably, such drug delivery systems are biodegradable, and are capable of being injected or surgically placed within the anterior or posterior segment of the mammalian eye.

In one embodiment, a sustained-release intraocular drug delivery system comprises a therapeutic agent, a polymeric carrier and a release modifier associated with the therapeutic agent to permit the therapeutic agent to be released into the interior of an eye of an individual for at least about one week after the drug delivery system is placed in the eye. The polymeric carrier can be a solid biodegradable polymeric material such as a PLA, a PLGA or a mixture thereof, or a viscous, polymeric biodegradable carrier such as a hyaluronic acid or a hyaluronate. The release modifier can be a long chain fatty alcohols. The long chain fatty alcohol must be incorporated into our sustained-release intraocular drug delivery system at a temperature above their melt temperature (or in a cosolvent solution with polymer) in order to fill voids in the solid (anhydrous) polymer matrix. A hyaluronic acid-based polymers is not a preferred polymeric biodegradable carrier because hyaluronic acid-based polymers are hydrogels that degrade (depolymerize) upon heating. Preferably, the polymeric carrier comprises a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof.

A method of making the present systems involves combining or mixing the therapeutic agent with the polymeric carrier to form a mixture. The mixture may then be extruded or compressed to form a single composition. The single composition may then be processed to form individual implants or microparticles suitable for placement in an eye of a patient. Solid implants suitable for use in our invention can be formed from polymer-drug blends by such methods as thermal extrusion, solvent casting, or direct compression. Our invention requires a molecular mixture of polymer and a release modifier such as fatty alcohol. Hence a compression method for making an implant is useful only if heat is applied to melt the polymeric matrix.

The implants can be placed in an ocular region to treat a variety of ocular conditions. Placement of the implants may be through surgical implantation, or through the use of an implant delivery device which administers the implant via a needle or catheter. The implants can effectively treat conditions associated with neovascularization of the eye, such as the retina. The therapeutic agent can be released at controlled or predetermined rates when the implant is placed in the eye. Such rates may range from about 0.003 micrograms/day to about 5000 micrograms/day.

Our invention encompasses a sustained release drug delivery system which comprises a water soluble therapeutic agent, a polymeric carrier for the therapeutic agent, and a release modifier for modifying a release rate of the therapeutic agent from the polymeric carrier. The release modifier is an aliphatic alcohol. This sustained release drug delivery system can release a therapeutic amount of the therapeutic agent over a period of time of at least about one week.

The water soluble therapeutic agent in our sustained release drug delivery system can be a protein or a polynucleotide, and the polymeric carrier can be a biodegradable polymer. Thus, the polymeric carrier can be a poly-lactide-co-glycolide (PLGA) polymer. Preferably, the aliphatic alcohol release modifier is long chain fatty alcohol, that is a long chain fatty alcohol which comprises from 10 to 40 carbon atoms.

Our sustained release drug delivery system exhibits a substantially linear rate of release of the therapeutic agent in vivo over a period of about 50 days. By substantially linear rate of release it is meant that the therapeutic agent is released from the polymeric carrier under does not vary by more than about 100% over the desired period of time, more usually by not more than about 50%.

The sustained release drug delivery system can release less that about 30% of the therapeutic agent after about 5 days in vivo and less that about 80% of the therapeutic agent after about 50 days in vivo.

A preferred embodiment of our sustained release drug delivery system can comprise (a) a water soluble therapeutic agent, wherein the water soluble therapeutic agent is a protein or a polynucleotide; (b) a biodegradable polymeric carrier associated with the therapeutic agent, and; (c) a release modifier, wherein the release modifier has the formula $R-(CH_2)_n-OH$, where n is an integer between 8 and 40 and R is selected from the group consisting of $CH_3-$, a cyclic compound (such as a four or five carbon cyclic compound), a polycyclic compound and an aromatic (such as a benzyl group) compound, wherein the sustained release drug delivery system can release a therapeutic amount of the therapeutic agent over a period of time of at least about one week.

The release modifier can be capryl alcohol, pelargonic alcohol, capric alcohol, lauryl alcohol, myristyl alcohol, cetyl alcohol, palmitoleyl alcohol, stearyl alcohol, isostearyl alcohol, elaidyl alcohol, oleyl alcohol, linoleyl alcohol, polyunsaturated elaidolinoleyl alcohol, polyunsaturated linolenyl alcohol, elaidolinolenyl alcohol, polyunsaturated ricinoleyl alcohol, arachidyl alcohol, behenyl alcohol, erucyl alcohol, lignoceryl alcohol, ceryl alcohol, montanyl alcohol, cluytyl alcohol, myricyl alcohol, melissyl alcohol, and/or geddyl alcohol.

Significantly, the sustained release drug delivery system can comprise a polymeric carrier which is a viscous aqueous carrier as opposed to a solid polymeric carrier. If a solid polymeric carrier it can be a poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof.

Our invention also includes a method for treating an ocular condition by intraocular placement of a sustained release drug delivery system comprising: (a) a water soluble therapeutic agent; (b) a polymeric carrier for the therapeutic agent, and; (c) a release modifier for modifying a release rate of the therapeutic agent from the polymeric carrier, wherein the release modifier is an aliphatic alcohol, and the sustained release drug delivery system can release a therapeutic amount of the therapeutic agent over a period of time of at least about one week. The step of intraocular placement is carrier out using an intraocular injector, such as using any of the injectors disclosed in U.S. Pat. Nos. 6,899,717; 7,090,681 or in U.S. patent application Ser. Nos. 10/917,909, 11/021,947.

The ocular condition can be, for example, uveitis, macular edema, macular degeneration, proliferative retinopathy, diabetic retinopathy, retinitis pigmentosa and/or glaucoma.

DESCRIPTION

We have discovered that sustained release of a water soluble therapeutic agent from a drug delivery device can be achieved by formulating the water soluble drug with a polymeric carrier and certain release modifiers. The release modifier is preferably an aliphatic (i.e. long chain) fatty alcohol.

Injectable or implantable sustained release dosage forms containing a water soluble drug substances typically exhibit a large initial burst release of the drug followed by very low drug release levels. The present invention encompasses use of long-chain fatty alcohols to modify the release profile of water soluble drugs from injectable and implantable sustained release systems. These release modifiers have no or a very low cytotoxicity.

The drug delivery system can be formulated as a solid polymeric implant or as a viscous injectable solution or dispersion. A formulation within the scope of our invention can comprise a drug, a polymeric carrier for the drug and a long-chain fatty alcohol release modifier. The drug delivery system can also comprise one or more additional drugs, polymer blends, fatty alcohol blends and excipients.

The fatty alcohols can have any chain length greater than about 6 carbon atoms, be straight chain or branched, saturated or unsaturated. We have found that saturated straight chain alcohols comprising 16 to 26 carbons are especially useful.

The drug delivery system can be in the form of a rod, tablet, capsule, sphere, microsphere, particle, sheet, filament, plaque or the like. The drug delivery system be present in a fluid vehicle for injection. Additionally, drug delivery system can be made by heat extrusion, cold press, solvent casting, melt casting, solvent evaporation and other known procedures.

A preferred release modifier is a biocompatible long chain fatty alcohol, such as 1-eicosanol, which is shown below:

$CH_3(CH_2)_{18}CH_2OH$

More preferred long-chain fatty alcohols are not branched and have from 16-26 carbons.

cholesterol

Cholesterol ($C_{27}H_{45}OH$), and and PEG-3350 [HO($C_2H_4O)_n$, a synthetic polyglycol having an average molecular weight of 3350], can both be considered to be long chain fatty alcohols, but these two particular long chain fatty alcohols are excluded from the scope of our invention because we determined through experiment that they are not suitable release modifier to use in the drug delivery systems disclosed herein.

Without intending to be bound by theory we can hypothesize that a long chain fatty alcohol can have utility as a release modifier in the drug delivery systems disclosed herein because these waxy molecules are particularly effective at blocking many of the pores and voids that are known to be present in a polymeric matrix. This blocking effect can be related to the melting points of our preferred fatty alcohols which are near or below the glass transition temperature for PLGA-type polymers, i.e., typically about 75-100° C. Melting points for the above listed fatty alcohols are as follows: 56° C. for C16; 57° C. for C18, 65° C. for C20, and 69° C. for C22. In effect, melted fatty alcohol may serve as "mortar" between the polymer "bricks". In the case of highly water-soluble compounds such as SIRNA-027, pores and voids allow water to permeate the matrix, thereby rapidly dissolving the encapsulated drug. While cholesterol is a fatty alcohol, the melt point is much too high (148° C.) to allow flow into these voids and pores. The long chain fatty alcohols useful as release modifiers in our invention are slowly removed from pores on the surface of our disclosed polymeric implant drug delivery systems since they are at least poorly water-soluble, and diffusion-limited drug release can continue as required.

Preferred release modifiers can be a long-chain fatty alcohols such as 1-hexadecanol (cetyl alcohol; C16), 1-octadecanol (stearyl alcohol; C18), 1-eicosanol (arachidyl alcohol; C20), and 1-docosanol (behenyl alcohol; C22). A fatty alcohol with an aliphatic chain shorter than about 14, for example 10 or less carbon atoms is sufficiently more water-soluble, meaning that it will be removed too quickly from the administered polymeric implant and is therefore not suitable for use in our drug delivery systems.

Controlled and sustained administration of one or more therapeutic agents through the use of our intraocular drug delivery systems, such as intraocular implants or polymeric particles, can effectively treat one or more ocular conditions. The present drug delivery systems comprise a pharmaceutically acceptable polymeric carrier and are formulated to release one or more pharmaceutically active agents over an extended period of time, such as for more than one week, and in certain embodiments for a period of time of one year or more. Thus, the present drug delivery systems can comprise a polymeric carrier for a water soluble drug, the water soluble drug (therapeutic agent), and a release modifier. The polymeric carrier can comprise one or more biodegradable polymers, one or more biodegradable copolymers, one or more non-biodegradable polymers, and one or more non-biodegradable copolymers, and combinations thereof. The polymeric carrier is a drug release sustaining component. The therapeutic agent of the present drug delivery systems is a water soluble therapeutic agents. Examples of water soluble therapeutic agents include peptides, proteins, nucleic acids, antibodies, and antibody fragments. For example, the therapeutic agent of the present drug delivery systems can comprise, consist essentially of, or consist entirely of, one or more therapeutic agents selected from the group consisting of anti-angiogenesis compounds, ocular hemorrhage treatment compounds, macromolecular non-steroidal anti-inflammatory agents, growth factor inhibitors (e.g. VEGF inhibitors), growth factors, cytokines, antibodies, oligonucleotide aptamers, antisense oligonucleotides small interfering ribonucleic acid (siRNA) molecules and antibiotics. The present drug delivery systems are effective to provide a therapeutically effective dosage(s) of the agent or agents directly to a region of the eye to treat, prevent, and/or reduce one or more symptoms of one or more undesirable ocular conditions. Thus, with each administration therapeutic agents are made available at the ocular site where they are needed and will be maintained at effective concentrations for an extended period of time, rather than subjecting the patient to more frequent injections or, in the case of self-administered drops, ineffective treatment with only limited bursts of exposure to the active agent or agents or, in the case of systemic administration, higher systemic exposure and concomitant side effects or, in the case of non-sustained release dosages, potentially toxic transient high tissue concentrations associated with pulsed, non-sustained release dosing.

A controlled drug release is achieved by an improved formulation of slow release biodegradable implants. The release rate of a drug from an implant is modulated by addition of a release modulator to the implant. The release modulator is a long chain (8-40 carbon atoms) fatty alcohol which is physiologically inert.

The rate of release of the therapeutic agent can be controlled by the rate of transport of the therapeutic agent through the polymeric matrix of the carrier, porosity of the polymeric matrix and the action of the release modifier. By modulating the release rate, the therapeutic agent is released at a substantially constant rate, or within a therapeutic dosage range, over the desired period of time. The rate of release will usually not vary by more than about 100% over the desired period of time, more usually by not more than about 50%. The therapeutic agent is made available to the specific site(s) where the agent is needed, and it is maintained at an effective dosage. The transport of drug through the polymer barrier can also be affected by drug solubility, polymer hydrophilicity, extent of polymer cross-linking, expansion of the polymer upon water absorption so as to make the polymer barrier more permeable to the drug, geometry of the implant, and the like.

The release modifier alters the release of a drug from a biodegradable implant in a defined manner. The release modifier is a release retardant. Formulations of particular interest can have a therapeutic combination of two or more active water soluble therapeutic agents, which provides for a sustained release of the agents.

In a preferred embodiment the present invention comprises an intraocular drug delivery system comprising a therapeutic agent comprising an anti-angiogenic and/or a neuroprotectant polypeptide, a polymeric carrier and a long chain fatty alcohol as a release modifier. Even more preferably, the present invention comprises at least a portion of a naturally occurring or synthetic antibody or antibody mimic having the ability to inhibit human VEGF activity. In one specific embodiment the therapeutic agent comprises a humanized anti-VEGF antibody, or fragment thereof, including a Fab fragment.

In another preferred embodiment the present invention comprises an intraocular drug delivery system that results in the intraocular administration of a therapeutic agent comprising an RNAi oligonucleotide (which may be double stranded) able to inhibit the translation of at least one VEGF or VEGFR mRNA species. In a particularly preferred embodiment the RNAi molecule comprises an siRNA oligonucleotide. In another preferred embodiment the siRNA is able to silence the expression of the VEGFR-2 receptor in a target cell. The antiVEGF-2 siRNA may comprise, for example, the following nucleotide sequences and their complementary oligonucleotide sequences, preferably their exact complements.

Preferably, though not exclusively, the polymeric carrier comprises a biodegradable polymer. The polymeric carrier may be understood to be a drug release sustaining component. The polymeric carrier can be joined to the therapeutic agent covalently, or the therapeutic agent may be dispersed within a matrix comprising the polymeric carrier.

A sustained-release intraocular drug delivery system in accordance with the present disclosure comprises a therapeutic agent, a polymeric carrier and a release modifier associated with the therapeutic agent to permit the therapeutic agent to be released into the interior of an eye of an individual for at least about one week after the drug delivery system is placed in the eye. In certain embodiments disclosed herein, the therapeutic agent can be released for at least about ninety days after placement in an eye, and may even be released for at least about one year after placement in the eye. The present drug delivery systems can provide targeted delivery of macromolecule therapeutic agents to intraocular tissues, such as the retina, while overcoming problems associated with conventional drug delivery methods, such as intraocular injection of non-sustained release compositions.

Definitions

For the purposes of this description, we use the following terms as defined in this section, unless the context of the word indicates a different meaning.

"About" means plus or minus ten percent of the number, range or item so qualified.

"Intraocular drug delivery system" means a device structured, sized, or otherwise configured to be placed in an eye. The present drug delivery systems are generally biocompatible with physiological conditions of an eye and do not cause unacceptable or undesirable adverse side effects. The present drug delivery systems are placed in an eye without disrupting vision. The present drug delivery systems can be in the form of a plurality of particles, such as microparticles, or may be in the form of implants, which are larger in size than the present particles.

"Therapeutic agent" means a protein or a polynucleotide useful for treating an ocular condition.

"Associated with" means mixed with, dispersed within, coupled to, covering, or surrounding.

"Ocular region" or "ocular site" means any area of the eye, including the anterior and posterior segment of the eye, and which generally includes, but is not limited to, any functional (e.g., for vision) or structural tissues found in the eyeball, or tissues or cellular layers that partly or completely line the interior or exterior of the eyeball. Ocular regions include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Biodegradable polymer" means to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The words "biodegradable" and "bioerodible" are equivalent and are used interchangeably herein. A biodegradable polymer may be a homopolymer, a copolymer, or a polymer comprising more than two different polymeric units.

"Treat", "treating", or "treatment" means reduction or resolution or prevention of an ocular condition, ocular injury or damage, or to promote healing of injured or damaged ocular tissue.

"Therapeutically effective amount" means the level or amount of agent needed to treat an ocular condition, or reduce or prevent ocular injury or damage without causing significant negative or adverse side effects to the eye or a region of the eye.

Intraocular drug delivery systems have been developed which can release drug loads over various time periods. These systems, which when placed into an eye of an individual, such as the vitreous of an eye, provide therapeutic levels of a therapeutic agent for extended periods of time (e.g., for about one week or more). In certain embodiments, the therapeutic agent is selected from the group consisting of anti-angiogenesis compounds, particularly anti-VEGF recombinant antibodies and antibody fragments such as ranibizumab and bevacizumab, ocular hemorrhage treatment compounds, non-steroidal anti-inflammatory agents, growth factor (e.g. VEGF) inhibitors, growth factors, cytokines, antibodies, oligonucleotide aptamers, siRNA molecules and antibiotics. The disclosed systems are effective in treating ocular conditions, such as posterior ocular conditions, such as glaucoma, retinal neurodegeneration, and neovascularization, and generally improving or maintaining vision in an eye.

The polymeric carrier of the present systems can comprise a biodegradable polymer. In certain embodiments, the therapeutic agent is associated with the polymeric carrier as a plurality of biodegradable particles. Such particles are smaller than the implants disclosed herein, and may vary in shape. For example, certain embodiments of the present invention utilize substantially spherical particles. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurement.

In other embodiments, the therapeutic agent is associated with the polymeric carrier as a biodegradable implant. In one embodiment of the present invention, an intraocular implant comprises a biodegradable polymer matrix. The biodegradable polymer matrix is one type of a drug release-sustaining component. The biodegradable intraocular implant comprises a therapeutic agent associated with the biodegradable polymer matrix. The matrix degrades at a rate effective to sustain release of an amount of the therapeutic agent for a time greater than about one week from the time in which the implant is placed in ocular region or ocular site, such as the vitreous of an eye.

In certain embodiments, the therapeutic agent of the present drug delivery systems is selected from the group consisting of anti-bacterial agents, anti-angiogenic agents, anti-inflammatory agents, neuroprotectant agents, growth factor inhibitors, such as VEGF inhibitors, growth factors, cytokines, intraocular pressure reducing agents, ocular hemorrhage therapeutic agents, and the like. The therapeutic agent may be any anti-angiogenic macromolecule, any ocular hemorrhage treatment macromolecule, any non-steroidal anti-inflammatory macromolecule, any VEGF inhibitory macromolecule, any peptide or oligonucleotides-containing growth factor, any cytokine, or any peptide or oligonucleotide antibiotic that can be identified and/or obtained using routine chemical screening and synthesis techniques. For example, the macromolecule therapeutic agent may comprise an agent or region selected from the group consisting of peptides, proteins, antibodies, antibody fragments (such as, without limitation, Fab fragments), and nucleic acids. Some examples include hyaluronidase (ocular hemorrhage treatment compound), ranibizumab (Lucentis®), pegaptanib (Macugen), and VEGF inhibitors) inhibiting fragments thereof, bevacizumab (Avastin®) and VEGF inhibiting fragments thereof, pegaptanib (Macugen®) and VEGF inhibiting fragments thereof, rapamycin, cyclosporine and RNAi gene silencing oligonucleotides, such as anti-VEGFR-2 inhibitory RNAi and the RNAi oligonucleotides described elsewhere in this specification.

In certain embodiments, the therapeutic agent of the present drug delivery systems comprises a short or small interfering ribonucleic acid (siRNA) or an oligonucleotide aptamer. For example, and in some preferred embodiments, the siRNA has a nucleotide sequence that is effective in inhibiting cellular production of vascular endothelial growth factor (VEGF) or VEGF receptors.

One specific example of a useful siRNA is available from Acuity Pharmaceuticals (Pennsylvania) or Avecia Biotechnology under the name Cand5. Cand5 is a therapeutic agent that essentially silences the genes that produce VEGF. Thus, drug delivery systems including an siRNA selective for VEGF can prevent or reduce VEGF production in a patient in need thereof.

As mentioned above, another example of a useful siRNA is available from Sirna Therapeutics (Colorado) under the name siRNA Z. siRNA Z is a chemically modified short interfering RNA (siRNA) that targets vascular endothelial growth factor receptor-1 (VEGFR-1). Some additional examples of nucleic acid molecules that modulate the synthesis, expression and/or stability of an mRNA encoding one or more receptors of vascular endothelial growth factor are disclosed in U.S. Pat. No. 6,818,447 (Pavco).

Other embodiments of the present systems may comprise an antibody selected from the group consisting of anti-VEGF antibodies, anti-VEGF receptor antibodies, anti-integrin antibodies, therapeutically effective fragments thereof, and combinations thereof.

Antibodies useful in the present systems include antibody fragments, such as Fab', F(ab)$_2$, Fabc, and Fv fragments. The antibody fragments may either be produced by the modification of whole antibodies or those synthesized de novo using recombinant DNA methodologies, and further include "humanized" antibodies made by now conventional techniques. The present systems can also comprise rapamycin (sirolimus). Rapamycin is a peptide that functions as an antibiotic, an immunosuppressive agent, and an anti-angiogenic agent.

Our drug delivery systems may also include salts of the therapeutic agents when appropriate. Pharmaceutically acceptable acid addition salts are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

The polymeric carrier of the present drug delivery systems can comprise a polymer selected from the group consisting of biodegradable polymers, non-biodegradable polymers, biodegradable copolymers, non-biodegradable copolymers, and combinations thereof. In certain preferred embodiments, the polymer is selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof.

The present drug delivery systems may be in the form of a solid element, a semisolid element, or a viscoelastic element, or combinations thereof. For example, the present systems may comprise one or more solid, semisolid, and/or viscoelastic implants or microparticles.

The therapeutic agent may be in a particulate or powder form and entrapped by a biodegradable polymer matrix. Usually, therapeutic agent particles in intraocular implants will have an effective average size less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric carrier, the resulting polymeric intraocular particles may be used to provide a desired therapeutic effect.

The therapeutic agent of the present systems is preferably from about 1% to 90% by weight of the drug delivery system. More preferably, the therapeutic agent is from about 5% to about 15% by weight of the system. In a preferred embodiment, the therapeutic agent comprises about 10% by weight of the system. In another embodiment, the therapeutic agent comprises about 20% by weight of the system.

The release modifier of the present systems is preferably from about 1% to 30% by weight of the drug delivery system. More preferably, the release modifier is from about 3% to about 20% by weight of the system. In a preferred embodiment, the release modifier comprises from about 5% to about 15% by weight of the system. In a particularly preferred embodiment of the present invention the therapeutic agent comprises about from about 5% to about 10% by weight of the drug delivery system.

Suitable polymeric materials or compositions for use in the implant include those materials which are compatible, that is biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic agent, ease of use of the polymer in making the drug delivery systems of the present invention, a half-life in the physiological environment of at least about 6 hours, preferably greater than about one day, not significantly increasing the viscosity of the vitreous, and water insolubility.

Also important to controlling the biodegradation of the polymer and hence the extended release profile of the drug delivery systems is the relative average molecular weight of the polymeric carried employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix of the present systems can comprise a mixture of two or more biodegradable polymers. For example, the system may comprise a mixture of a first biodegradable polymer and a different second biodegradable polymer. One or more of the biodegradable polymers can have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric carrier of the present systems is associated with the therapeutic agent so that the release of the therapeutic agent into the eye is by one or more of diffusion, erosion, dissolution, and osmosis. As discussed herein, the matrix of an intraocular drug delivery system may release drug at a rate effective to sustain release of an amount of the therapeutic agent for more than one week after implantation into an eye. In certain systems, therapeutic amounts of the therapeutic agent are released for more than about one month, and even for about twelve months or more. For example, the therapeutic agent can be released into the eye for a time period from about ninety days to about one year after the system is placed in the interior of an eye.

The release of the therapeutic agent from the intraocular systems comprising a biodegradable polymer matrix may include an initial burst of release followed by a gradual increase in the amount of the therapeutic agent released, or the release may include an initial delay in release of the therapeutic agent followed by an increase in release. When the system is substantially completely degraded, the percent of the therapeutic agent that has been released is about one hundred. Compared to existing implants, the systems disclosed herein do not completely release, or release about 100% of the therapeutic agent, until after about one week of being placed in an eye.

It may be desirable to provide a relatively constant rate of release of the therapeutic agent from the drug delivery system over the life of the system. For example, it may be desirable for the therapeutic agent to be released in amounts from about 0.01 µg to about 2 µg per day for the life of the system. However, the release rate may change to either increase or decrease depending on the formulation of the biodegradable polymer matrix. In addition, the release profile of the therapeutic agent may include one or more linear portions and/or one or more non-linear portions. Preferably, the release rate is greater than zero once the system has begun to degrade or erode.

As discussed in the examples herein, the present drug delivery systems comprise a therapeutic agent, a polymeric carrier and a release modifier associated to release an amount of the therapeutic agent that is effective in providing a concentration of the therapeutic agent in the vitreous of the eye in a range from about 0.2 nM to about 5 µM. In addition or alternatively, the present systems can release a therapeutically effective amount of the macromolecule at a rate from about 0.003 µg/day to about 5000 µg/day. The desired release rate and target drug concentration can vary depending on the particular therapeutic agent chosen for the drug delivery system, the ocular condition being treated, and the patient's health. Optimization of the desired target drug concentration and release rate can be determined using routine methods known to persons of ordinary skill in the art.

The drug delivery systems, such as the intraocular implants, can be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic agent, including the therapeutic agent(s) described herein, can be distributed in a non-homogenous pattern in the matrix. For example, the drug delivery system may include a portion that has a greater concentration of the therapeutic agent relative to a second portion of the system. The present drug delivery systems can be in the form of solid implants, semi-solid implants, and viscoelastic implants, as discussed herein.

The intraocular implants disclosed herein can have a size of between about 5 µm and about 2 mm, or between about 10 µm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants can also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. However, larger implants may also be formed and further processed before administration to an eye. In addition, larger implants may be desirable where relatively greater amounts of a therapeutic agent are provided in the implant, as discussed in the examples herein. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems can be of any geometry including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the system can also be used to control the rate of release, period of treatment, and drug concentration at the site of implantation. For example, larger implants will deliver a proportionately larger dose, but depending on the surface to mass ratio, may have a slower release rate. The particular size and geometry of the system are chosen to suit the site of implantation.

The proportions of therapeutic agent, polymer, and the release modifier can be empirically determined by formulating several implants, for example, with varying proportions of such ingredients. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

The amount of active agent or agents employed in the drug delivery system, individually or in combination, will vary widely depending on the effective dosage required and the desired rate of release from the system. As indicated herein, the agent will be at least about 1, more usually at least about 10 weight percent of the system, and usually not more than about 80.

In addition to the therapeutic agent, the intraocular drug delivery systems disclosed herein may include an excipient component, such as effective amounts of buffering agents, and antioxidants to protect a drug (the therapeutic agent) from the effects of ionizing radiation ($\alpha$ or $\beta$) during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

Release modifiers are disclosed in U.S. Pat. No. 5,869,079. The amount of release modulator employed will be dependent on the desired release profile, the activity of the modulator, and on the release profile of the therapeutic agent in the absence of modulator. Electrolytes such as sodium chloride and potassium chloride may also be included in the systems. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In one embodiment our intravitreal drug delivery system can comprise a biodegradable polymer, such as PLGA, and a VEGFNEGFR (particularly ranibizumab or bevacizumab or VEGF-inhibiting derivatives or fragments of either of these). The system can be in the form of a biodegradable intravitreal implant, or a population of biodegradable polymeric microparticles. The drug delivery system includes an amount of a VEGFNEGFR inhibitor that when released from the system, the inhibitor can provide a therapeutic effect. For example, the biodegradable implant can comprise a peptide, a nucleic acid molecule, a protein, or other agent that interferes with interactions between VEGF and VEGFR. Examples of useful inhibitors are described above. These drug delivery systems provide prolonged delivery of the VEGF inhibitor directly into the vitreous of an eye in need of treatment. Thus, these drug delivery systems can provide effective treatment of one or more ocular conditions, including without limitation, neovascularization, ocular tumors, and the like.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

The present drug delivery systems are preferably administered to patients in a sterile form. For example, the present drug delivery systems, or compositions containing such systems, may be sterile when stored. Any routine suitable method of sterilization may be employed to sterilize the drug delivery systems. For example, the present systems may be sterilized using radiation. Preferably, the sterilization method does not reduce the activity or biological or therapeutic activity of the therapeutic agents of the present systems. Sterilization by heat or gas (ethylene oxide) is not used for our drug delivery systems since the former sterilization method can result in polymer degradation and deformation and the latter sterilization method can result in formation or deposit of unacceptable chemical residues. The only practical sterilization method for use for our drug delivery systems is by gamma or beta irradiation, with the beta irradiation being preferred due to less heat buildup.

Various techniques may be employed to produce the drug delivery systems described herein. Useful techniques include, but are not necessarily limited to, solvent evaporation methods, phase separation methods, interfacial methods, molding methods, injection molding methods, thermal extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C. In addition, the implant may be coextruded so that a coating is formed over a core region during the manufacture of the implant.

Compression methods may be used to make the drug delivery systems, and typically yield elements with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The present systems may be configured to release the therapeutic agent into the eye at a rate from about 0.003 μg/day to about 5000 μg/day. Thus, the foregoing methods may combine the polymeric carrier and the therapeutic agent to form a drug delivery system with such desirable release rates. In addition, the present systems can be configured to provide amounts of the macromolecule therapeutic agent that are cleared from the vitreous at a desired target rate. As described in the examples, the clearance rates can range from about 3 mL/day to about 15 mL/day. However, certain implants can release therapeutically effective amounts of the macromolecule therapeutic agent that are cleared from the vitreous at lower rates, such as less than about 1 mL/day. For example, Gaudreault et al. ("Preclinical pharmacokinetics of ranibizumab (rhuFabV2) after a single intravitreal administration", IOVS, (2005); 46(2):726-733) reports that ranibizumab can be cleared from the vitreous at rates of about 0.5 to about 0.7 mL/day when a ranibizumab formulation is intravitreally injected.

The present systems can be formed by extruding a polymeric carrier/therapeutic agent mixture without disrupting the biological activity of the macromolecule therapeutic agent. For example, implants have been invented which include a macromolecule that retains its structure after an extrusion process. Thus, in spite of the manufacturing conditions, drug delivery systems in accordance with the disclosure herein have been invented which include biologically active macromolecules.

The drug delivery systems of the present invention can be inserted into the eye, for example the vitreous chamber of the eye, by a variety of methods, including intravitreal injection or surgical implantation. For example, the drug delivery systems may be placed in the eye using forceps or a trocar after making a 2-3 mm incision in the sclera. Preferably, the present systems can be placed in an eye without making an incision. For example, the present systems may be placed in an eye by inserting a trocar or other delivery device directly through the eye without an incision. The removal of the device after the placement of the system in the eye can result in a self-sealing opening. One example of a device that may be used to insert the implants into an eye is disclosed in U.S. patent publication 2004/0054374. The method of placement may influence the therapeutic agent or drug release kinetics. For example, delivering the system with a trocar may result in placement of the system deeper within the vitreous than placement by forceps, which may result in the system being closer to the edge of the vitreous. The location of the system may influence the concentration gradients of therapeutic agent or drug surrounding the element, and thus influence the release rates (e.g., an element placed closer to the edge of the vitreous may result in a slower release rate).

Ocular conditions treatable using the drug delivery systems disclosed herein include: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpiginous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant is administered to a posterior segment of an eye of a human or animal patient, and preferably, a living human or animal. In at least one embodiment, an implant is administered without accessing the subretinal space of the eye. However, in other embodiments the implant may be inserted into the subretinal space. For example, a method of treating a patient may include placing the implant directly into the posterior chamber of the eye. In other embodiments, a method of treating a patient may comprise administering an implant to the patient by at least one of intravitreal placement, subretinal placement, subconjunctival placement, sub-tenon placement, retrobulbar placement, and suprachoroidal placement. Placement methods may include injection and/or surgical insertion.

In at least one embodiment, a method of reducing neovascularization or angiogenesis in a patient comprises administering one or more implants containing one or more therapeutic agents, as disclosed herein to a patient by at least one of intravitreal injection, subconjunctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the therapeutic agent from the implants.

EXAMPLES

The following examples illustrate aspect and embodiments of the present invention and are not intended to limit the scope of our invention.

Example 1

Manufacture and Testing of a Sustained Release Drug Delivery System with a Release Modifier Biodegradable implants are made by combining about 10-20% by weight of a therapeutic agent, such as those agents described above, about with 70-85% by weight of a biodegradable polymeric carrier, and about 5-10% by weight of a long chain fatty alcohol release modifier in a stainless steel mortar. The release modifier can be an aliphatic alcohol such as capryl alcohol, pelargonic alcohol, capric alcohol, lauryl alcohol, myristyl alcohol, cetyl alcohol, palmitoleyl alcohol, stearyl alcohol, isostearyl alcohol, elaidyl alcohol, oleyl alcohol, linoleyl alcohol, polyunsaturated elaidolinoleyl alcohol, polyunsaturated linolenyl alcohol, polyunsaturated elaidolinolenyl alcohol, polyunsaturated ricinoleyl alcohol, arachidyl alcohol, erucyl alcohol, lignoceryl alcohol, ceryl alcohol, montanyl alcohol, cluytyl alcohol, myricyl alcohol, melissyl alcohol and geddyl alcohol. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 µg and 1100 µg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 µg and 1100 µg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7, 14, 28, and every two weeks thereafter.

Drug assays may be performed by HPLC, which consists of a Waters 2690 Separation Module (or 2696), and a Waters 2996 Photodiode Array Detector. An Ultrasphere, C-18 (2), 5 mm; 4.6×150 mm column heated at 30° C. can be used for separation and the detector can be set at 264 nm. The mobile phase can be (10:90) MeOH—buffered mobile phase with a flow rate of 1 mL/min and a total run time of 12 min per sample. The buffered mobile phase may comprise (68:0.75:0.25:31) 13 mM 1-Heptane Sulfonic Acid, sodium salt—glacial acetic acid—triethylamine—Methanol. The release rates can be determined by calculating the amount of drug being released in a given volume of medium over time in mg/day.

The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 2

Preparation and Therapeutic Use of an Anti-VEGF Extended Release Implant(s)

VEGF (Vascular Endothelial Growth Factor) (also known as VEGF-A) is a growth factor which can stimulate vascular endothelial cell growth, survival, and proliferation. VEGF is believed to play a central role in the development of new blood vessels (angiogenesis) and the survival of immature blood vessels (vascular maintenance). Tumor expression of VEGF can lead to the development and maintenance of a vascular network, which promotes tumor growth and metastasis. Thus, increased VEGF expression correlates with poor prognosis in many tumor types. Inhibition of VEGF can be an anticancer therapy used alone or to complement current therapeutic modalities (eg, radiation, chemotherapy, targeted biologic therapies).

An extended release bioerodible implant system can be used to treat an ocular condition mediated by a VEGF. Thus, the implant can contain as active agent a VEGF inhibitor. For example, either ranibizumab (Lucentis®;rhuFab V2) (or bevacizumab (Avastin®; rhuMab-VEGF), both made by Genentech, South San Francisco, Calif.), and the implant(s) an be made using the method of Example 1. Ranibizumab and bevacizumab are both anti-VEGF (vascular endothelial growth factor) antibody products that may have particular utility for patients with macular degeneration, including the wet form of age-related macular degeneration. The implant or implants can be loaded with a total of about 50 to about 500 µg or more of the ranibizumab (i.e. about 150 µg of ranibizumab can be loaded into the implants prepared according to the Example 1 method). Bevacizumab is approved as an antiangiogenic for the treatment of colorectal cancer at a concentration of 1 mg/ml. However, it is currently being divided by pharmacists into small portions (approximately 50 µl to approximately 100 µl in volume) for intravitreal injection. The use of Avastin® for age-related macular degeneration would benefit from inclusion into a extended release implant system in accordance with the present invention. In addition, one or more implant device may be injected into the eye to deliver a higher amount of the drug than would otherwise be given. Ranibizumab is a humanized Fab, and a derivative of the humanized anti-VEGF synthetic IgG1 bevacizumab. It will be understood that with regard to its inclusion into an implant or drug delivery system according to the present invention, reference to ranibizumab in the examples of this specification is substantially equally applicable to, and shall constitute a disclosure of the use in the same manner of, bevacizumab.

The ranibizumab (or bevacizumab) extended release implant system or systems can be implanted into an ocular region or site (i.e. into the vitreous) of a patient with an ocular condition for a desired therapeutic effect. The implant(s) can be inserted into the vitreous using the procedure (trocar implantation) as described herein, or by incision. The implant(s) can release a therapeutic amount of the ranibizumab for an extended period of time, such as for one 1 month, or 2 months, or 3 months, or 4 months or 5 months or more, or even more than six months, to thereby treat a symptom of the ocular condition.

An extended release bioerodible intraocular implant for treating an ocular condition, such as an ocular tumor can also be made as set forth in Example 1, using about 1-3 mg of the VEGF Trap compound available from Regeneron, Tarrytown, N.Y.

Example 3

Polymeric Drug Delivery Systems Containing siRNA Z

Drug delivery systems which comprise about 86.1 milligrams of siRNA Z can be made using the process of Example 1. Such drug delivery systems can release siRNA Z at a rate of from about 49.7 micrograms per day to about 4970 micrograms per day. The release rates can be measured using in vitro and/or in vivo assays as described above. Placement of the siRNA Z drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 4

Manufacture and Testing of Implants Containing Sustained Release Drug Delivery System with Various Long Chain Fatty Alcohol a Release Modifiers We made and tested PLGA implant filaments designed for the sustained release of a therapeutic agent, such as a therapeutic polynucleotide. Each implant made weighed about 400 mg. To made the implants, freeze-dried oligonucleotide (23-mer ONT; 40 mg or 10% w/w) was blended separately with the one of the excipient fatty alcohols used; cholesterol, polyethylene glycol 3350 (PEG-3350) or 1-eicosanol. The fatty alcohol release modifier comprised 20 mg or 5% w/w of each non-control implant prepared. Powdered PLGA (Resomer RG-752, Boehringer Ingelheim) made up the remaining 85% by weight of the 400 mg non-control implants made. The blended powder (polynucleotide, release modifier and polymer resomer) was heated to about 77° C. and then processed into thin filaments using a piston extruder fitted with a 500 µm exit nozzle. Filaments were cut into segments (about 6 mm long) and incubated in tubes containing phosphate buffered saline (pH 7.4) using a shaker water bath set at 37° C. At selected time intervals, release media was removed for ONT analysis by reverse-phase HPLC and fresh release media was added.

Figure 1:
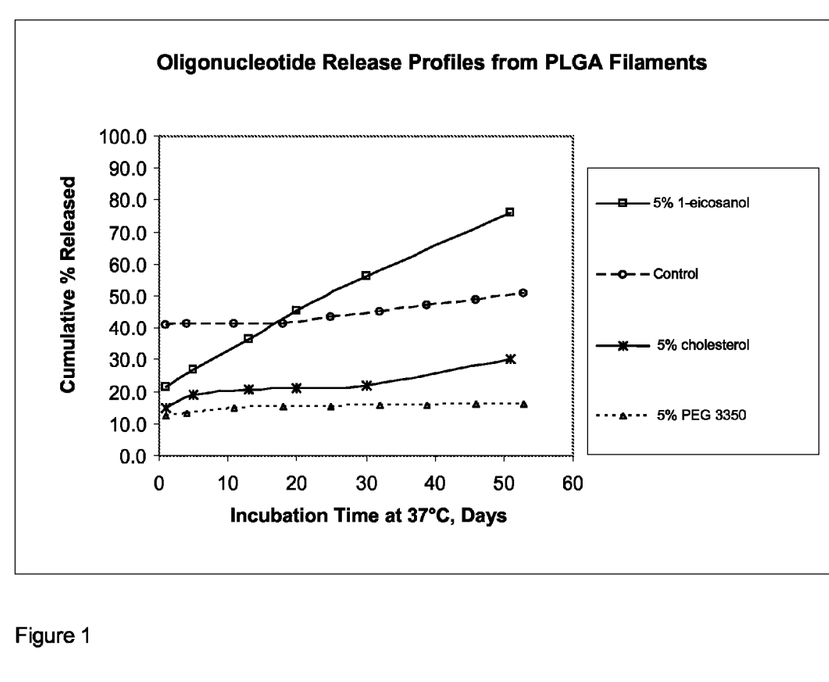
FIG. 1 is a graph cumulative % in vitro release of the polynucleotide 23-mer ONT from a PLGA sustained release drug delivery system ("DDS") upon formulation of the DDS with one of three different release modifiers (1-eicosanol, cholesterol, and PEG 3350) as compared to cumulative % in vitro release of the polynucleotide 23-mer ONT from the same DDS formulated without a release modifier.

All tested excipients (the release modifiers) used in this experiment were waxy solids at room temperature. Control PLGA 400 mg filaments (90% w/w PLGA and 10% w/w the ONT; no release modifier present in the controls) exhibited unacceptably high burst release of ONT (over 40% after 24 hours). Cholesterol and the polyethylene glycol 3350 (PEG-3350) effectively blocked burst release, but subsequent release rates were extremely low for about 30 days and would not result in a therapeutic level of ONT in the target tissue. As shown by FIG. 1, unexpectedly, the filaments containing the 1-eicosanol release modifier showed a low burst release followed by an almost linear, diffusion-controlled release lasting at least 50 days.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A sustained release, biodegradable intraocular implant comprising
   a) about 70-85% by weight of a biodegradable polymeric carrier, wherein the biodegradable polymeric carrier is a poly-lactide-co-glycolide (PLGA) co-polymer;
   b) about 10-20% by weight of a water soluble therapeutic agent, wherein the therapeutic agent is an inhibitor of vascular endothelial growth factor (VEGF) selected from the group consisting of ranibizumab, bevacizumab, mixtures of ranibizumab and bevacizumab, pegaptanib, and an siRNA molecule; and c) about 5-10% by weight of a long chain fatty alcohol comprising from between 10 to 40 carbon atoms;

wherein a therapeutically effective amount of the therapeutic agent is released from the biodegradable intraocular implant for at least one week after the intraocular implant is placed in the eye.

2. The intraocular implant of claim 1, wherein the long chain fatty alcohol is selected from the group consisting of capric alcohol, lauryl alcohol, myristyl alcohol, cetyl alcohol, palmitoleyl alcohol, stearyl alcohol, isostearyl alcohol, elaidyl alcohol, oleyl alcohol, linoleyl alcohol, polyunsaturated elaidolinoleyl alcohol, polyunsaturated linolenyl alcohol, elaidolinolenyl alcohol, polyunsaturated ricinoleyl alcohol, arachidyl alcohol, behenyl alcohol, erucyl alcohol, lignoceryl alcohol, ceryl alcohol, montanyl alcohol, cluytyl alcohol, myricyl alcohol, melissyl alcohol, and geddyl alcohol.

3. A method for treating an ocular condition, the method comprising the step of intraocular placement of a sustained release, biodegradable intraocular implant according to claim 1.

4. The method of claim 3, wherein the step of intraocular placement is carried out using an intraocular injector.

5. The method of claim 3, wherein the ocular condition is selected from the group consisting of uveitis, macular edema, macular degeneration, proliferative retinopathy, diabetic retinopathy, retinitis pigmentosa and glaucoma.

6. The intraocular implant of claim 1, wherein said long chain fatty alcohol is selected from the group consisting of 1-hexadecanol, 1-octadecanol, and 1-eicosanol.

7. The intraocular implant of claim 1, wherein said long chain fatty alcohol is a saturated straight chain alcohol 16 to 26 carbon atoms in length.

8. The intraocular implant of claim 1, wherein said long chain fatty alcohol is 1-eicosanol.

* * * * *

UNITED STATES PATENT AND TRADEMARK OFFICE
CERTIFICATE OF CORRECTION

PATENT NO. : 8,039,010 B2
APPLICATION NO. : 11/556503
DATED : October 18, 2011
INVENTOR(S) : John T. Trogden et al.

It is certified that error appears in the above-identified patent and that said Letters Patent is hereby corrected as shown below:

On the Title page, in field (56), under "Other Publications", in column 2, line 8, delete "Opthalmology" and insert -- Ophthalmology --, therefor.

On the Title page, in field (56), under "Other Publications", in column 2, line 30, delete "olignucleotide" and insert -- oligonucleotide --, therefor.

In column 3, line 2, after "well" delete "a".

In column 7, line 40-55, below "carbons." delete "  ".

In column 7, line 57, delete "and and" and insert -- and and --, therefor.

In column 18, line 43, delete "VEGFNEGFR" and insert -- VEGF/VEGFR --, therefor.

Signed and Sealed this
Sixth Day of December, 2011

David J. Kappos
*Director of the United States Patent and Trademark Office*

In column 18, line 48, delete "VEGFNEGFR" and insert -- VEGF/VEGFR --, therefor.